(12) United States Patent
Pan et al.

(10) Patent No.: US 10,398,367 B2
(45) Date of Patent: Sep. 3, 2019

(54) INTERACTIVE DEVICE AND METHOD

(71) Applicant: HON HAI PRECISION INDUSTRY CO., LTD., New Taipei (TW)

(72) Inventors: Hung-Yu Pan, New Taipei (TW); Fu-Yen Hsieh, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 358 days.

(21) Appl. No.: 15/186,561

(22) Filed: Jun. 20, 2016

(65) Prior Publication Data

US 2017/0311861 A1 Nov. 2, 2017

(30) Foreign Application Priority Data

Apr. 27, 2016 (CN) .......................... 2016 1 0270862

(51) Int. Cl.
| A61B 5/16 | (2006.01) |
| A61B 5/024 | (2006.01) |
| A61B 5/00 | (2006.01) |
| G08B 5/36 | (2006.01) |
| A61B 5/021 | (2006.01) |
| A61B 5/08 | (2006.01) |

(52) U.S. Cl.
CPC .......... *A61B 5/165* (2013.01); *A61B 5/02444* (2013.01); *A61B 5/486* (2013.01); *A61B 5/742* (2013.01); *G08B 5/36* (2013.01); *A61B 5/021* (2013.01); *A61B 5/02416* (2013.01); *A61B 5/02438* (2013.01); *A61B 5/0816* (2013.01)

(58) Field of Classification Search
None
See application file for complete search history.

(56) References Cited

U.S. PATENT DOCUMENTS

| 9,064,390 | B1 * | 6/2015 | Clark | ........................ | G08B 5/36 |
| 2009/0128487 | A1 * | 5/2009 | Langereis | ............ | A61B 5/0205 |
| | | | | | 345/157 |
| 2012/0280951 | A1 * | 11/2012 | Bychkov | ................ | G06Q 50/24 |
| | | | | | 345/184 |
| 2014/0107493 | A1 * | 4/2014 | Yuen | ..................... | H04W 4/027 |
| | | | | | 600/473 |

* cited by examiner

Primary Examiner — Pascal M Bui Pho
Assistant Examiner — Colin T. Sakamoto
(74) Attorney, Agent, or Firm — ScienBiziP, P.C.

(57) ABSTRACT

A mood-conscious interaction device detects at least one physiological data of a user, and turns on a light with a color which corresponds to the physiological data. Thus, other users can know a mood or emotion of the user according to the color of the light, and the moods or emotion of the other users can be made known to the user during communications.

7 Claims, 3 Drawing Sheets

INTERACTIVE DEVICE AND METHOD

CROSS-REFERENCE TO RELATED APPLICATIONS

This application claims priority to Chinese Patent Application No. 201610270862.5 filed on Apr. 27, 2016.

FIELD

The subject matter herein generally relates to personal communications, and particularly to an interaction device and method.

BACKGROUND

Users usually interact with others via internet by using text, image, video, and audio. Users cannot generally know the mood of other users during the interaction, the effects of communication between users are affected.

BRIEF DESCRIPTION OF THE DRAWINGS

Implementations of the present technology will now be described, by way of example only, with reference to the attached figures.

DETAILED DESCRIPTION

Figure 1:
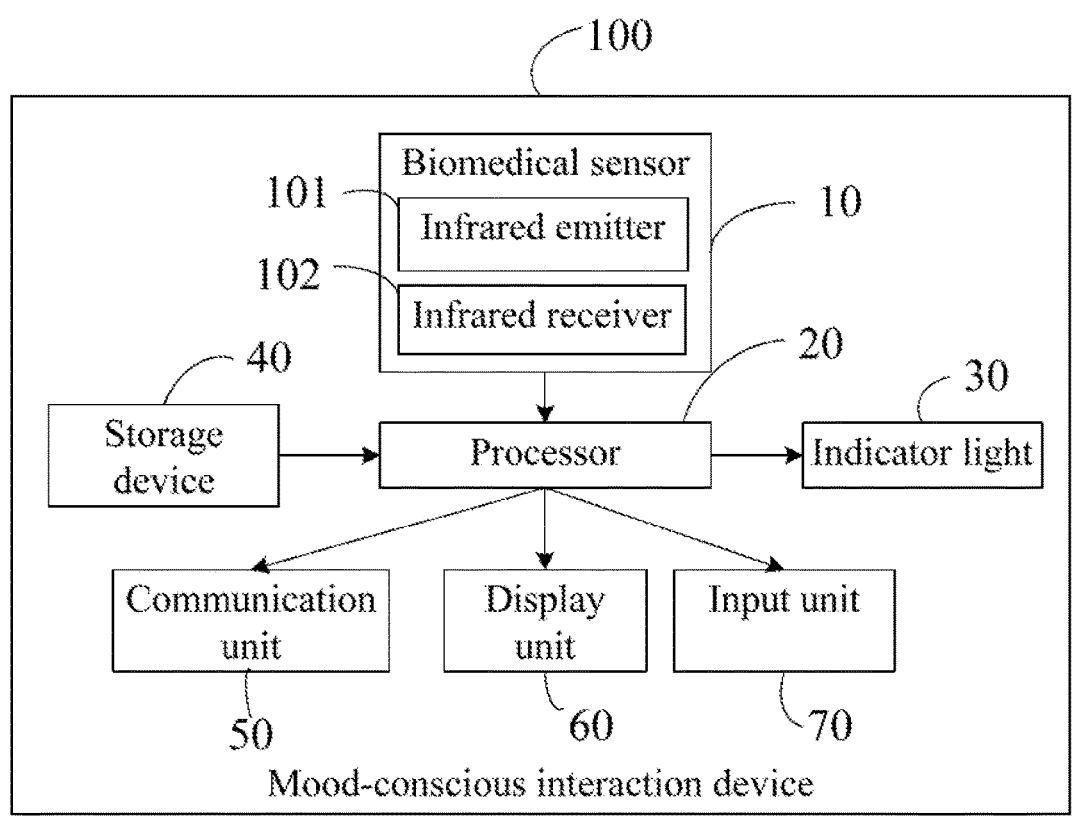
FIG. 1 is a block diagram illustrating an embodiment of a mood-conscious interaction device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

The term "comprising" means "including, but not necessarily limited to", it specifically indicates open-ended inclusion or membership in a so-described combination, group, series and the like.

FIG. 1 illustrates an embodiment of a mood-conscious interaction device 100 (hereinafter "interaction device 100"). In the exemplary embodiment, the interaction device 100 at least includes a biomedical sensor 10, a processor 20, a number of indicator lights 30, and a storage device 40. The indicator lights 30 have different colors. The biomedical sensor 10 detects physiological data of a user, such as heart rate, blood pressure, respiratory rate. The storage device 40 stores a first relationship between a number of physiological data ranges and a number of colors of the indicator lights. The processor 20 determines which color of the indicator lights 30 should be turned on, according to the detected physiological data and the first relationship stored in the storage device 40. Then the processor 20 controls one indicator light 30 having the determined color to turn on, to indicate the emotion or mood of the user.

In the exemplary embodiment, the interaction device 100 can be, but is not limited to, a smart wearable device, such as a smart watch, a smart necklace, a smart clothing, smart glasses, and the like. In an alternative embodiment, the interaction device 100 can be, but is not limited to, a portable electronic device, such as a smart phone, a portable computer, or the like. In other embodiments, the interaction device 100 further can be, but is not limited to, decorative lights arranged in a room. Users can press their fingers or wrist against the biomedical sensor 10 arranged in the decorative lights, the color of the decorative lights can change according to the physiological data of the user as detected by the biomedical sensor 10. The mood of the room can thus be changed, and other people in the room become more aware of the emotion of the user.

In the exemplary embodiment, the biomedical sensor 10 is a heart rate sensor which includes an infrared emitter 101 and an infrared receiver 102. The infrared emitter 101 faces the infrared receiver 102. When a user puts a finger between the infrared emitter 101 and the infrared receiver 102, the infrared emitter 101 emits infrared ray toward the infrared receiver 102, the infrared ray passes through the finger and is received by the infrared receiver 102. When the infrared ray passes through the finger, the pulsing of blood vessel of the finger blocks the infrared ray propagation which leads to the infrared receiver 102 receiving changeable infrared ray. The infrared receiver 102 detects the heart rate of the user according to the changes of the received infrared ray.

In an alternative embodiment, the biomedical sensor 10 further can be an existing pulse sensor, a respiration sensor, or a sphygmomanometer, but is not limited thereto.

In the exemplary embodiment, the biomedical sensor 10 and the indicator lights 30 are arranged in a same device. In other embodiments, the biomedical sensor 10 and the indicator lights 30 can be arranged in different devices, for example, the indicator light 30 can be a decorative light and the biomedical sensor 10 can be arranged in a smart phone. The biomedical sensor 10 detects the user's physiological data and transmits the detected physiological data to the decorative light, then the decorative light changes color accordingly.

In the exemplary embodiment, the indicator lights 30 are light emitting diodes (LEDs). Each indicator light 30 can include a translucent lampshade, thus the light emitted by the indicator lights 30 will softer. In this embodiment, three lights are taken as the indicator lights 30 as an example to describe the disclosure. The colors of the three indicator lights 30 are respectively red, yellow, and green.

The storage device 40 stores the first relationship between a number of physiological data ranges and a number of colors of the indicator lights 30. In the embodiment, taking heart rate N as an example to describe the disclosure, where a unit of the heart rate is beats per minute. The first relationship between the physiological data ranges and the colors of the indicator lights 30 include: the heart rate range $N \geq 85$ can correspond to a red light, which indicates that the user is very agitated, for example the user is very happy or very angry; the heart rate range $75 \leq N < 85$ can correspond to the yellow light, which indicates that the user feels unsettled, for example the user feels a bit happy or a bit angry; the heart rate range $60 \leq N < 75$ can correspond to the green light, which indicates the user is calm and stable.

Figure 2:
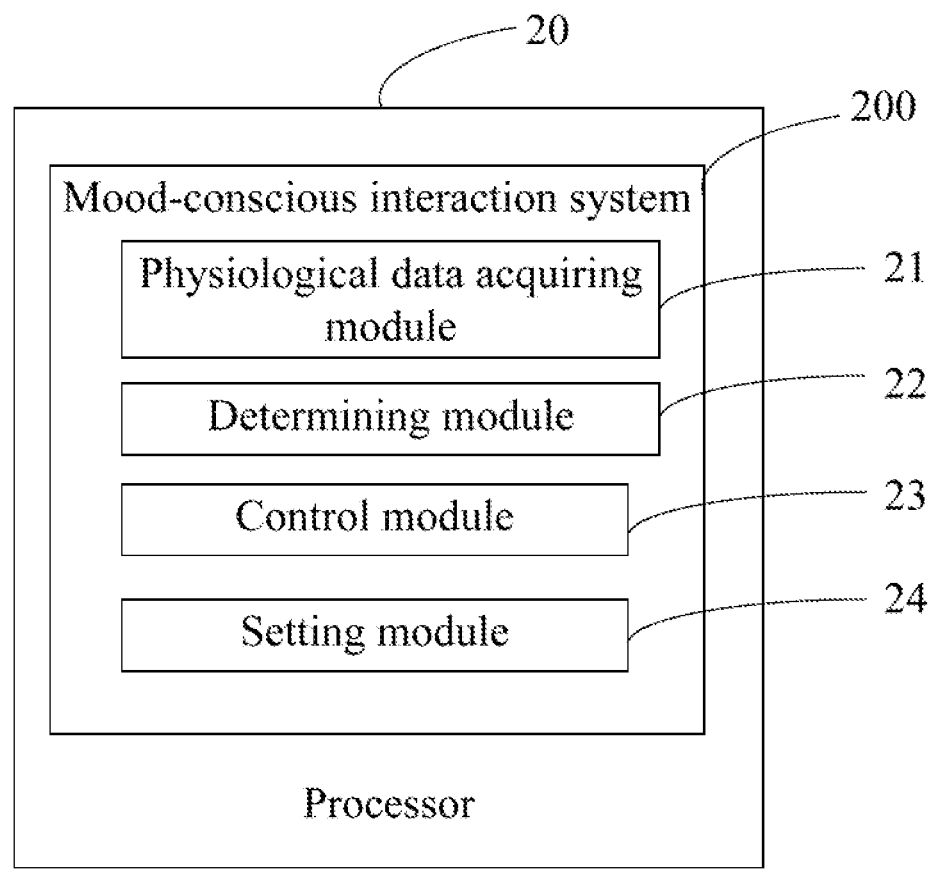
FIG. 2 is a block diagram illustrating an embodiment of a mood-conscious interaction system running in the mood-conscious interaction device of FIG. 1.

FIG. 2 illustrates a mood-conscious interaction system 200 running in the interaction device 100. In the embodiment, the mood-conscious interaction system 200 includes a number of modules, which are collections of software instructions stored in the storage device 40 and executed by the processor 20. In the embodiment, the modules can include at least a physiological data acquiring module 21, a determining module 22, and a control module 23. In the embodiment, the processor 20 can be a central processing unit, a micro processor, or other data processing chip. The storage device 40 can be a smart media card, a secure digital card, a hard disk, a flash memory, or a compact disk, for example.

The physiological data acquiring module 21 acquires physiological data from the biomedical sensor 10.

The determining module 22 determines which color of the indicator lights 30 should be turned on according to the physiological data and the first relationship stored in the storage device 40.

The control module 23 controls the indicator light 30 having the determined color to turn on.

In the embodiment, the mood-conscious interaction system 200 further includes a setting module 24 for the user to set a first relationship between the physiological data and the colors of the indicator lights 30.

In an alternative embodiment, the indicator lights 30 further can include several light groups, each light group corresponding to one user. In the embodiment, each light group includes a number of lights which have different colors. The storage device 40 further stores identify information of a number of users and a second relationship between the identities of the users and the light groups, thus different light groups can indicate different user's emotion.

In the exemplary embodiment, the interaction device 100 further can include a communication unit 50. The interaction device 100 can communicate with other mood-conscious interaction devices via the communication unit 50. In detail, the interaction device 100 transmits the physiological data detected by the biomedical sensor 10 to other interaction devices via the communication unit 50, or transmits a turning on command in relation to indicator lights 30 to other interaction devices via the communication unit 50. In this embodiment, the turning on command in relation to indicator lights 30 transmitted to other devices is configured to turn on the indicator lights of other devices which having the same color as the turning on indicator lights 30 of the interaction device 100. Thus, other interaction devices can obtain and display visual evidence of the emotion of the user of the interaction device 100.

In the exemplary embodiment, the interaction device 100 further includes a display unit 60. The display unit 60 can be a touch input screen. The communication unit 50 can receive physiological data and/or the turning on command of the indicator lights from other interaction devices, and the display unit 60 displays the respective emotions of the users of other interaction devices according to mood-conscious commands received. In this embodiment, the display unit 60 can display the emotions of a number of users.

In the exemplary embodiment, the interaction device 100 further includes an input unit 70. In this embodiment, the display unit 60 and the input unit 70 can be integrated in a touch input screen. The display unit 60 further can display an interactive interface for the users to communicate with others. The input unit 70 is configured for the users to input information, such as voice, characters, and/or videos.

In the exemplary embodiment, the interaction device 100 further can communicate with other interaction devices to form a social network. Users of the interaction devices in the social network can add friends, chat in groups, and the like.

In the exemplary embodiment, the interaction device 100 further can upload the physiological data detected by the biomedical sensor 10 to a cloud server. Thus the uploaded physiological data can be used in many other fields, for example in medical system.

Figure 3:
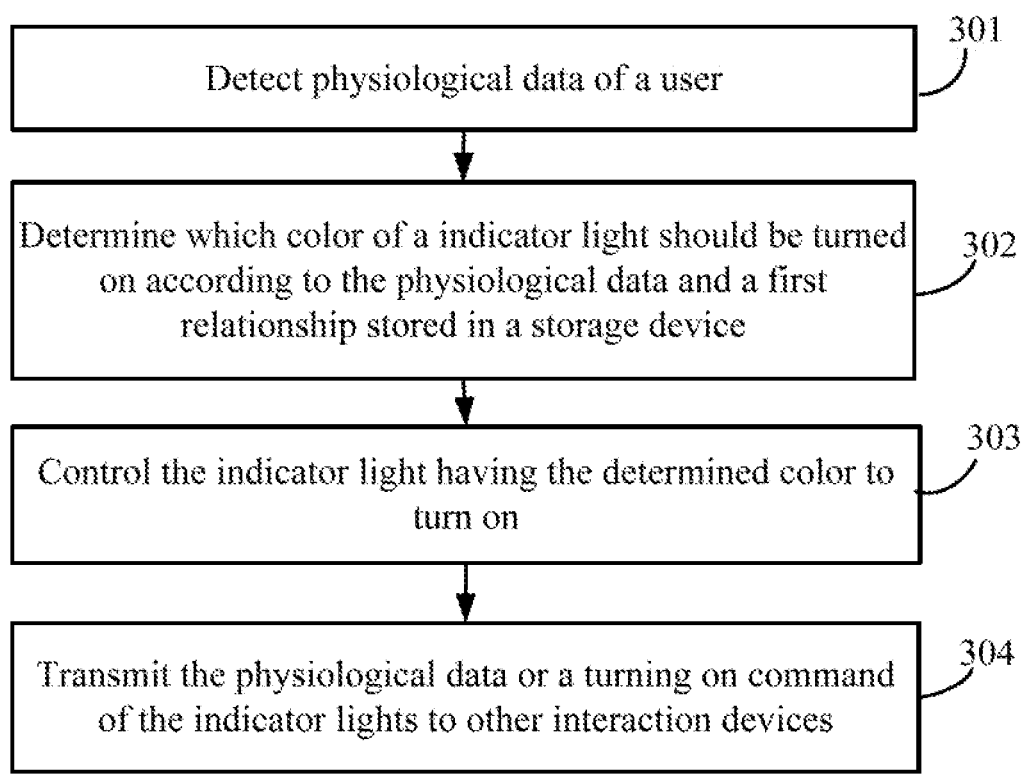
FIG. 3 is a flowchart illustrating an embodiment of a mood-conscious interaction method.

FIG. 3 illustrates a mood-conscious interaction method. The method is provided by way of example, as there are a variety of ways to carry out the method. The method described below can be carried out using the configurations illustrated in FIG. 1, for example, and various elements of these figures are referenced in explaining the example method. Each block shown in FIG. 3 represents one or more processes, methods, or subroutines carried out in the example method. Additionally, the illustrated order of blocks is by example only and the order of the blocks can be changed. The example method can begin at block 301.

At block 301, a biomedical sensor detects physiological data of a user.

At block 302, a processor determines which color of a indicator light should be turned on according to the physiological data and a first relationship between a number of physiological data ranges and a number of colors of the indicator lights.

At block 303, the processor controls the indicator light having the determined color to turn on.

In the exemplary embodiment, the method further includes block 304: a communication unit transmits the physiological data or a turning on command in relation to the indicator lights to other interaction devices.

In the exemplary embodiment, the method further can include:
a display unit displaying an interactive interface; and
an input unit receiving user input in the interactive interface.

In the exemplary embodiment, the method further includes: the communication unit uploading the physiological data to a cloud server.

It is believed that the present embodiments and their advantages will be understood from the foregoing description, and it will be apparent that various changes may be made thereto without departing from the spirit and scope of the disclosure or sacrificing all of its material advantages, the examples hereinbefore described merely being exemplary embodiments of the present disclosure.

What is claimed is:

1. An interactive method for indicating a first mood of a first user and a second mood of a second user, the method comprising:
  providing the first user with a first interactive device, wherein the first interactive device comprises:
    a first biomedical sensor configured to detect first physiological data of the first user,
    a first plurality of indicator lights, each having a different respective color of a plurality of colors,
    a first processor, and
    a first storage device having stored thereon a first relationship between a plurality of physiological data ranges and the plurality of colors;
  providing the second user with a second interactive device, wherein the second interactive device comprises:
    a second biomedical sensor configured to detect second physiological data of the second user, and
    a second plurality of indicator lights, each having a different respective color of the plurality of colors;

acquiring the first physiological data detected by the first biomedical sensor;

identifying, by the first processor, a first color from the plurality of colors according to the acquired first physiological data and the first relationship;

controlling, by the first processor, one indicator light from the first plurality of indicator lights that has the identified first color to turn on, thereby indicating the first mood;

transmitting a first turning-on command from the first interactive device to the second interactive device, wherein the first turning-on command is configured to turn on an indicator light from the second plurality of indicator lights that has the identified color to indicate the first mood to the second user; and receiving, at the first interactive device, a second turning-on command originating from the second interactive device, wherein the second turning-on command is configured to turn on an indicator light from the first plurality of indicator lights that has a color corresponding to the second mood to indicate the second mood to the first user.

2. The interactive method according to claim 1, further comprising:

transmitting the first physiological data to the second interactive device; and receiving, at the first interactive device, the second physiological data from the second interactive device.

3. The interactive method according to claim 1, further comprising:

displaying an interactive interface; and receiving user inputs to the interactive interface.

4. The interactive method according to claim 1, wherein the first biomedical sensor is a heart rate sensor, wherein the heart rate sensor comprises an infrared emitter and an infrared receiver, the infrared emitter arranged to face the infrared receiver.

5. The interactive method according to claim 1, wherein the first plurality of indicator lights comprise several light groups respectively corresponding to several users including the first user and the second user, wherein each light group comprises a group of indicator lights each having a different respective color of the plurality of colors, the method further comprising:

storing, in the first storage device, identification information of the several users and a second relationship between the identification information of the several users and the several light groups.

6. The interactive method according to claim 2, wherein the first interactive device further comprises a display screen, the method further comprising:

displaying, on the display screen, the second mood according to the received second physiological data or the received second turning-on command.

7. The interactive method according to claim 1, wherein the first interactive device is a smart wearable device, a portable electronic device, or decorative lights.

* * * * *